(12) United States Patent
Damen et al.

(10) Patent No.: US 11,061,095 B2
(45) Date of Patent: Jul. 13, 2021

(54) SYSTEMS AND METHODS FOR $B_0$-CORRECTED ARTERIAL SPIN LABELING MAGNETIC RESONANCE IMAGING

(71) Applicant: THE BOARD OF TRUSTEES OF THE UNIVERSITY OF ILLINOIS, Urbana, IL (US)

(72) Inventors: Frederick C. Damen, Urbana, IL (US); Kejia Cai, Urbana, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 0 days.

(21) Appl. No.: 16/647,984

(22) PCT Filed: Sep. 26, 2018

(86) PCT No.: PCT/US2018/052954
§ 371 (c)(1),
(2) Date: Mar. 17, 2020

(87) PCT Pub. No.: WO2019/067615
PCT Pub. Date: Apr. 4, 2019

(65) Prior Publication Data
US 2020/0284864 A1 Sep. 10, 2020

Related U.S. Application Data

(60) Provisional application No. 62/563,122, filed on Sep. 26, 2017.

(51) Int. Cl.
*G01R 33/563* (2006.01)
*A61B 5/026* (2006.01)
(Continued)

(52) U.S. Cl.
CPC ...... *G01R 33/56333* (2013.01); *A61B 5/0263* (2013.01); *A61B 5/055* (2013.01);
(Continued)

(58) Field of Classification Search
CPC ........... G01R 33/56333; G01R 33/465; G01R 33/5608; G01R 33/56366; A61B 5/0263; A61B 5/055
See application file for complete search history.

(56) References Cited

U.S. PATENT DOCUMENTS

| | | | |
|---|---|---|---|
| 6,564,080 B1 * | 5/2003 | Kimura | A61B 5/0263 324/307 |
| 7,627,360 B2 * | 12/2009 | Kimura | A61B 5/0263 324/306 |

(Continued)

OTHER PUBLICATIONS

The International Search Report (ISR) with Written Opinion for PCT/US2018/052954 dated Jan. 25, 2019, pp. 1-13.
(Continued)

*Primary Examiner* — Dixomara Vargas
(74) *Attorney, Agent, or Firm* — McDonnell Boehnen Hulbert & Berghoff LLP

(57) ABSTRACT

Disclosed herein are systems and methods for correction of imaging-plane uniform magnetic field—($B_0$) inhomogeneity-induced magnetic resonance imaging (MRI) artifacts. The systems and methods can be implemented to improve the filtering and correction of arterial spin labeling (ASL) MRI data by forming a tagging dependent Z-spectrum (TADDZ) of ASL MRI data. In TADDZ, images are acquired via ASL, MRI after tagging blood water at a number of tagging, distances upstream and downstream of die MM system's imaging plane. A tagging distance dependent Z-spectrum is analyzed for each image to map the magnetic field inhomogeneity across the imaging plane. Along with magnetic-field mapping, Z-spectrum analysts
(Continued)

and data processing enables TADDZ to remove magnetic field inhomogeneity induced artifacts, resulting in more clear and clinically relevant perfusion imaging via MRI.

20 Claims, 8 Drawing Sheets

(51) Int. Cl.
*A61B 5/055* (2006.01)
*G01R 33/465* (2006.01)
*G01R 33/56* (2006.01)

(52) U.S. Cl.
CPC ....... *G01R 33/465* (2013.01); *G01R 33/5608* (2013.01); *G01R 33/56366* (2013.01)

(56) References Cited

U.S. PATENT DOCUMENTS

| | | | | |
|---|---|---|---|---|
| 9,084,554 | B2* | 7/2015 | Jung | A61B 5/02028 |
| 9,192,322 | B2* | 11/2015 | Wong | A61B 5/0042 |
| 10,561,337 | B2* | 2/2020 | Zhao | G01R 33/5611 |
| 2004/0030240 | A1* | 2/2004 | Kimura | G01R 33/563 |
| | | | | 600/420 |
| 2010/0240983 | A1* | 9/2010 | Jung | A61B 5/055 |
| | | | | 600/410 |
| 2012/0271157 | A1* | 10/2012 | Wong | A61B 5/0042 |
| | | | | 600/419 |
| 2015/0305645 | A1* | 10/2015 | Ouyang | G01R 33/56366 |
| | | | | 600/419 |
| 2016/0296126 | A1 | 10/2016 | Berry et al. | |
| 2017/0035319 | A1* | 2/2017 | Zhao | A61B 5/055 |

OTHER PUBLICATIONS

Damen, Frederick C. et al. "Tagging distance dependent Z-spectrum (TADDZ) for ASL MRI free from B0-inhomogeneity induced errors" Proceedings for the International Society for Magnetic Resonance in Medicine (2017), No. 3804, pp. 1-4.

Zhou, Jinyuan et al. "Amide Proton Transfer (APT) Contrast for Imaging of Brain Tumors" Magnetic Resonance in Medicine (2003) vol. 50, pp. 1120-1126.

Pekar, James et al. "Perfusion Imaging with Compensation for Asymmetric Magnetization Transfer Effects" Magnetic Resonance in Medicine (1996) vol. 35(1), pp. 70-79.

Luh, Wen-Ming et al. "Pseudo-Continuous Arterial Spin Labeling at 7 T for Human Brain: Estimation and Correction for Off-Resonance Effects Using a Prescan" Magnetic Resonance in Medicine (2013) vol. 69, pp. 402-410.

* cited by examiner

SYSTEMS AND METHODS FOR $B_0$-CORRECTED ARTERIAL SPIN LABELING MAGNETIC RESONANCE IMAGING

CROSS REFERENCE TO RELATED APPLICATIONS

This application is a U.S. national stage application under 35 U.S.C. § 371 of International Application No. PCT/US2018/052954, filed Sep. 26, 2018, which claims the benefit of U.S. Provisional Application No. 62/563,122, filed Sep. 26, 2017, the disclosures of which are incorporated by reference herein in their entireties.

FIELD OF THE INVENTION

This invention relates generally to improvements to magnetic resonance imaging; and in particular, to improvements to magnetic resonance imaging that eliminate $B_0$-inhomogeneity artifacts.

BACKGROUND

Magnetic resonance imaging (MRI) is commonly used to image the internal tissues of a subject.

An MRI system conventionally includes hardware components, including a plurality of gradient coils positioned about a bore of a magnet, an RF transceiver system, and an RF switch controlled by a pulse module to transmit RF pulses to and receive RF signals from an RF coil assembly. The received RF signals are also known as magnetic resonance (MR) signal data. An MRI system also conventionally includes a computer programmed to cause the system to apply to an object in the system various RF pulses, magnetic fields, and field gradients for inducing spin excitations and spatial encoding in an object, to acquire MR signal data from the object, to process the MR signal data, and to construct an MR image of the object from the processed MR signal data. The computer can include one or more general or special purpose processors, one or more forms of memory, and one or more hardware and/or software interfaces for interacting with and/or controlling other hardware components of the MRI system.

MRI is conventionally performed by placing the subject or object to be imaged at or near the isocenter of a strong, uniform magnetic field, $B_0$, known as the main magnetic field. The main magnetic field causes the atomic nuclei (spins) that possess a magnetic moment in the matter comprising the subject or object to become aligned in the magnetic field. The spins form a magnetization that precesses around the magnetic field direction at a rate proportional to the magnetic field strength. For hydrogen nuclei (which are the common nuclei employed in MRI), the precession frequency is approximately 64 MHz in a magnetic field of 1.5 Tesla. If the magnetization is perturbed by a small radio-frequency magnetic field, known as a $B_1$ magnetic field, the spins emit radiation at a characteristic radio frequency (RF). The emitted RF radiation can be detected and analyzed to yield information that can be used to produce an image of the subject or biologic material.

In practice, magnetic field gradients are also applied to the subject or object in addition to the main magnetic field. The field gradients are conventionally applied along one or more orthogonal axes, (x, y, z), the z-axis usually being aligned with the $B_0$, and introduce spatially distributed variations in frequency and/or phase of the precessing nuclear spins. By applying the radio-frequency $B_1$ magnetic field and gradient fields in carefully devised pulses and/or sequences of pulses that are switched on and off, the RF radiation emitted can carry spatially encoded information that, when detected and analyzed, can be used to produce detailed, high resolution images of the subject or object. Various techniques utilizing both specific pulse sequences and advanced image reconstruction methods have been developed, providing new advances, as well as introducing new challenges.

In order to enhance visualization of blood perfusion—particularly in the brain—techniques have been developed for increasing blood contrast using spatially selective RF pulses. For instance, in arterial spin labeled (ASL) MRI, pulses of RF radiation are used to "tag" blood in a tagging plane at an offset distance upstream of the imaging plane of the MRI system by inverting the magnetization of the blood relative to the surrounding biological material. When this magnetically tagged blood is imaged in the downstream imaging plane, the blood has greater contrast, allowing for better visualization of blood perfusion through the imaged biological material.

While ASL MRI can allow for enhanced visualization of blood flow, the applied RF tagging pulses have potential to introduce artifacts into the downstream imaging plane. For example, the same pulses used to magnetically tag the blood can also reduce signal from adjacent biological materials due to direct saturation (DS) and magnetization transfer (MT) effects. These effects are generally correlated with the distance between the tagging plane and the imaging plane (the "tagging distance"), and are the most pronounced when the tagging distance approaches zero (i.e., when the tagging plane is nearest the imaging plane). In conventional ASL MRI, these effects are controlled for by acquiring an additional control image. In the control image, the tagging RF pulse is applied to blood water at an equal tagging distance, but offset downstream of the imaging plane. In theory, equal amount of DS and MT artifacts will be seen in the control image, and can be removed by subtracting the control image from the tagged image.

This conventional ASL MRI technique works well when there is no static $B_0$ magnetic field inhomogeneity—however, this is rarely the case. Given that $B_0$ field is frequently inhomogeneous (often over 0.5 ppm) within the imaging plane, the DS and MT effects can vary disproportionately between the target and control images. Particularly for small tagging distances, imaging-plane $B_0$ magnetic field inhomogeneities can lead to large variations and errors in blood perfusion maps. Regional artifacts with hyperintensity can be misdiagnosed as hyperperfused lesions, such as tumors, while regional artifacts with hypointensity could be considered to be hypoperfused conditions like stroke. On the other hand, real cancer or stroke lesions can be masked in the presence of unfavorable $B_0$-inhomogeneity, leading to missed or delayed diagnosis. Such misdiagnoses can lead to the mistreatment or delayed treatment of patients, and can cause dramatic socioeconomic losses for health clinics and providers. Thus, enhanced imaging techniques are still desired for removing artifacts in ASL MRI under inhomogeneous $B_0$ magnetic field conditions.

SUMMARY

The aspects and embodiments disclosed herein are not limited to specific advantages or functionality.

In a first implementation, a method for imaging a target region of biologic material in an imaging plane is disclosed. The method is implemented in a magnetic resonance imaging (MRI) system having a $B_0$ magnetic field defining an axial scan direction. The method includes acquiring a set of arterial spin labeled (ASL) MRI target data of the target region. The target data is acquired using a first set of tagging distances positioned upstream of fluid flow toward the target region. The first set of tagging distances is offset from one another along the axial scan direction of the MRI system. The method further includes acquiring a set of ASL MRI control data of the target region. The control data is acquired using a second set of tagging distances positioned downstream of fluid flow from the target region. The second set of tagging distances is offset from one another along the axial scan direction of the MRI system. The method also includes generating Z-spectra of the target region of biologic material in the imaging plane based on at least the set of ASL MRI target data and the set of ASL MRI control data. The method additionally includes adjusting the Z-spectra by applying an estimated inhomogeneity of the B0 magnetic field. The method yet further includes generating a corrected image of the target region of the biologic material based on at least the adjusted Z-spectra.

In a second implementation, a non-transitory computer-readable medium is provided. The non-transitory computer-readable medium includes instructions stored thereon that. When executed by one or more processors or a magnetic resonance imaging (MRI) system having a $B_0$ magnetic field defining an axial scan direction, the instructions cause the MRI system to carry out operations. The operations include acquiring a set of arterial spin labeled (ASL) MRI target data of the target region. The target data is acquired using a first set of tagging distances positioned upstream of fluid flow toward the target region and offset from one another along the axial scan direction of the MRI system. The operations further include acquiring a set of ASL MRI control data of the target region. The control data is acquired using a second set of tagging distances positioned downstream of fluid flow from the target region and offset from one another along the axial scan direction of the MRI system. The operations also include generating Z-spectra of the target region of biologic material in the imaging plane based on at least the set of ASL MRI target data and the set of ASL MRI control data. The functions additionally include adjusting the Z-spectra by applying an estimated inhomogeneity of the B0 magnetic field. The functions yet further include generating a corrected image of the target region of the biologic material based on at least the adjusted Z-spectra.

In a third implementation, a magnetic resonance imaging (MRI) system is provided. The system includes a $B_0$ magnetic field defining an axial scan direction, one or more processors, a memory, and machine-readable instructions stored in the memory. When executed by the one or more processors, the instructions cause the system to carry out operations. The operations include acquiring a set of arterial spin labeled (ASL) MRI target data of the target region. The target data is acquired using a first set of tagging distances positioned upstream of fluid flow toward the target region and offset from one another along the axial scan direction of the MRI system. The operations further include acquiring a set of ASL MRI control data of the target region. The control data is acquired using a second set of tagging distances positioned downstream of fluid flow from the target region and offset from one another along the axial scan direction of the MRI system. The operations also include generating Z-spectra of the target region of biologic material in the imaging plane based on at least the set of ASL MRI target data and the set of ASL MRI control data. The operations additionally include adjusting the Z-spectra by applying an estimated inhomogeneity of the B0 magnetic field. The operations yet further include generating a corrected image of the target region of the biologic material based on at least the adjusted Z-spectra.

These and other features and advantages will be more fully understood from the following detailed description taken together with the accompanying claims.

BRIEF DESCRIPTION OF THE DRAWINGS

The following detailed description can be best understood when read in conjunction with the following drawings in which:

FIG. 1A: Conventional ASL contrast relies on the signal difference between images with and without signal from blood water attenuated. The image with blood water attenuated, called the tag image, is acquired after attenuating the blood water spins in the arteries prior to entering the imaging plane. Conventionally, a control image is acquired by tagging a plane located with equal distance but opposite direction from the imaging slice. Conventional ASL MRI works only when there is no static magnetic field ($B_0$) inhomogeneity. $G_{ad}$ is the ASL gradient. FIG. 1B: Under $B_0$ inhomogeneity, tagging offset frequencies of the control plane is not equivalent to that of the tagging plane, leading to $B_0$-inhomogeneity induced artifacts in the resulting CBF maps.

of the CBF maps within their row. The upper right image is a $T_2$-weighed image showing the brain anatomy.

Figure 8:
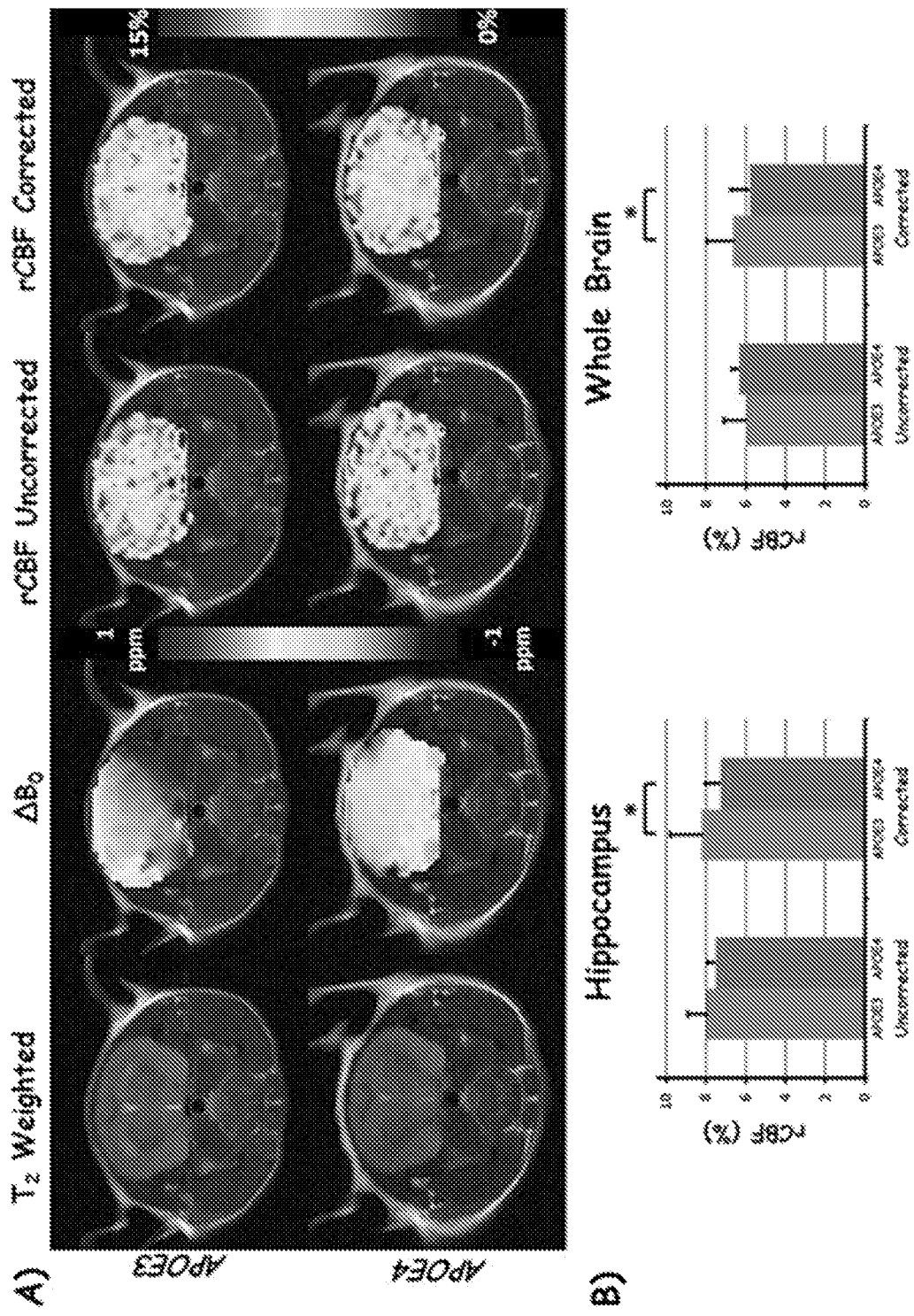

FIG. 8 shows TADDZ MRI produced $B_0$-corrected CBF maps that can differentiate the subtle CBF difference between ApoE-3 and ApoE-4 genotyped Alzheimer's disease (AD). (A) Representative brain images from an ApoE3, top row, and an ApoE4, bottom row, mouse. Columns from left to right are $T_2$ weighted image, $\Delta B_0$, uncorrected (from conventional ASL. MRI), and corrected rCBF maps (from TADDZ MRI), respectively. (B) Bar chart depiction of the rCBF differences between ApoE3 and ApoE4 mice, uncorrected (conventional ASL MRI, left) and corrected (TADDZ MRI, right) within the hippocampus (left chart) and whole brain (right chart). * p<0.05.

DETAILED DESCRIPTION

1. Overview

All publications, patents and patent applications cited herein are hereby expressly incorporated by reference for all purposes.

Perfusion, the delivery of oxygen and nutrient rich blood to tissue, is crucial to the health and wellbeing of tissue, especially in the brain. Accordingly, noninvasive perfusion imaging can be crucial to research and diagnosis of cerebral vascular conditions, such as stroke, brain cancer, neurodegenerative diseases, and other neurological disorders. MRI techniques for the visualization and quantification of cerebral blood flow (CBF) maps are becoming increasingly commonplace for research and clinical application. One such technique is arterial spin labeling (ASL) MRI, which uses exogenous arterial spin labeling to increase the contrast between blood water and surrounding tissue.

In ASL MRI, visualization of perfusion relies on the signal difference between images with and without the tagging of blood water to increase contrast. Contrast is achieved by attenuating the blood water signal with a spatially-selective RF pulse configured to invert the magnetization of the blood water. In order to provide selective contrast to the blood, RF pulses are applied to a tagging plane upstream of the imaging plane of the MRI system. This allows ASL MRI to attenuate the signal of the flowing blood at the tagging plane without substantially increasing contrast in tissues inside the imaging plane of the MRI system. The image with the blood water attenuated, hereinafter called the target image, is acquired after tagging the blood water by attenuating the blood water spins upstream, prior to entering the imaging plane. When this magnetically tagged blood water is imaged in the downstream imaging plane, the blood water has increased contrast relative to surrounding tissue, allowing for better visualization of perfusion through the target region of biologic material.

In additional to inverting the magnetization of blood water, the tagging RF pulses have potential to introduce artifacts into the imaging plane, leading to reduced signal-to-noise in the acquired image. For example, the RF pulses used to magnetically tag the blood water can also reduce signal from adjacent biological materials due to direct saturation (DS) and magnetization transfer (MT) effects. These effects are generally correlated with the tagging distance, and are the most pronounced when the tagging plane is near the imaging plane. As used herein, the term "tagging distance" is used to indicate the distance, or offset, between the imaging plane (i.e., the location of the target region of biological material being imaged by the MRI system) and a tagging plane (i.e., the location of the fluid being saturated by the tagging RF pulse) of the MRI system.

As described above, the target image is acquired after tagging blood water upstream of the imaging plane, such that the tagged blood then flows toward the biological material in the imaging plane. When the target image is acquired in the imaging plane, the blood water is visualized with increased contrast compared to the surrounding tissue, allowing for enhanced visualization of blood perfusion. However, artifacts introduced from the tagging RF pulse (e.g., DS and MT artifacts) may also be present in the target image of the biological material.

Figures 1A, 1B:
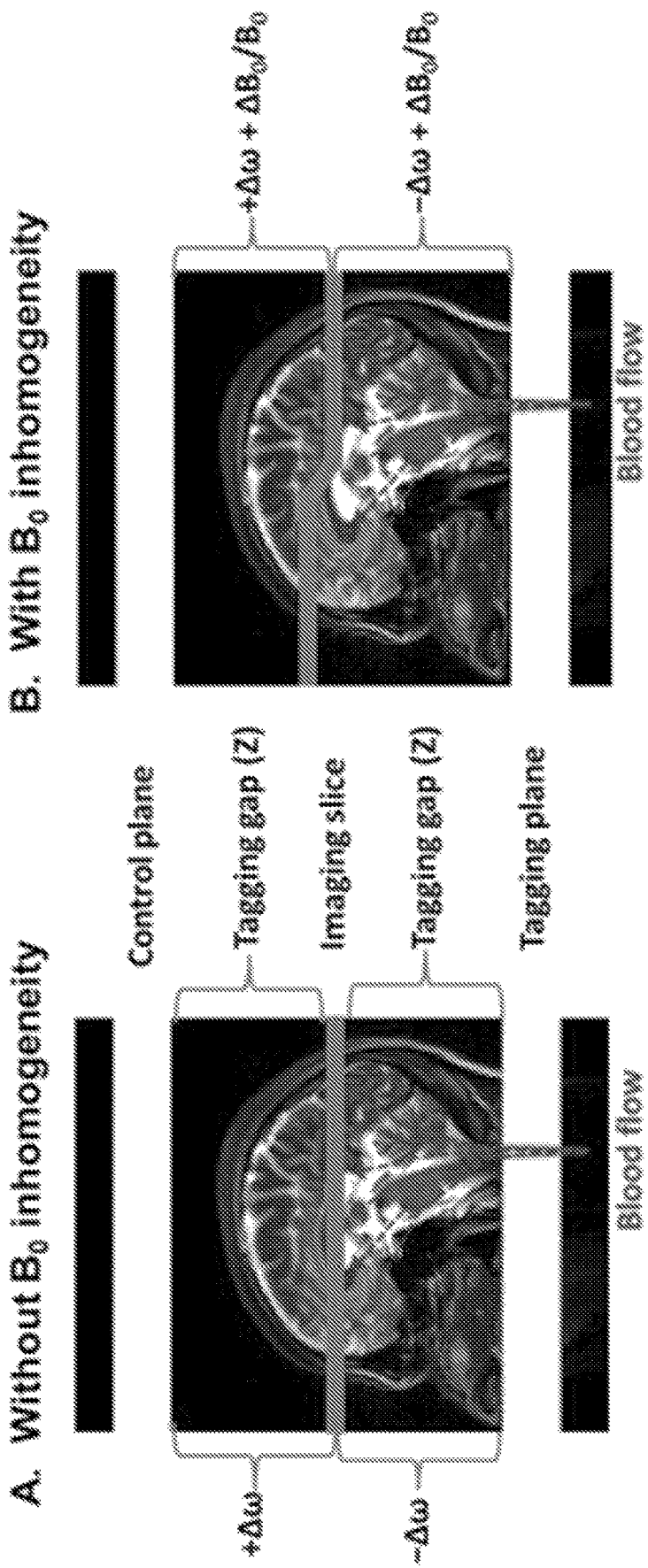
FIGS. 1A-B depict the concept of conventional ASL.

Accordingly, a control image can also be acquired by tagging in a control plane downstream of, and at an equal tagging offset from, the imaging plane. FIG. 1A shows an example configuration of the tagging and control planes of the tagging and control images, respectively, relative to the central imaging plane. In contrast with the tagging images, the control image is acquired after tagging downstream blood water flowing away from the biological material in the imaging plane. Accordingly, when the control image is acquired, the tagged blood is not present in the image. However, because the control image is acquired at an equal tagging distance downstream of the imaging plane, equivalent DS and MT artifacts from the tagging RF pulse in the control plane can be expected. When generating a conventional ASL MRI of the imaging plane, the control image is subtracted from the target image in order to selectively remove background tissue and artifacts, while allowing for visualization of the higher-contrast blood.

However, because the $B_0$ field in an MRI system is frequently inhomogeneous (often over 0.5 ppm) within the imaging plane, the DS and MT effects can vary disproportionately between the tag and control images. As seen in FIG. 1B, these magnetic field inhomogeneities can create regional artifacts that vary widely across the imaging plane. Thus, when target and control images of the imaging plane are used to image of a target region of tissue, these regional artifacts may be compounded, resulting in unpredictable CBF maps and potentially clinical misdiagnoses.

Disclosed herein are systems and methods for correction of imaging-plane magnetic field ($B_0$) inhomogeneity-induced magnetic resonance imaging (MRI) artifacts using tagging distance-dependent Z-spectra (TADDZ). Tagging distance dependent Z-spectral (TADDZ) MRI is an arterial spin labeling (ASL) imaging technique that reduces $B_0$-inhomogeneity artifacts in ASL MRI images by analyzing a plurality of ASL MRI images at varying tagging distances. The acquisition of multiples images allows TADDZ to produce a tagging-distance and/or frequency dependent Z-spectral image dataset, which can be used to estimate and accommodate for an inhomogeneous $B_0$ magnetic field in a MRI system.

TADDZ MRI methods can be applied to any magnetic field strength, any ASL sequence, and any biologic material, including the brain, spinal cord, heart, other organs, and other biologic matter. It features endogenous contrast, high spatial resolution, and reasonable temporal resolution (i.e., down to several minutes or less). TADDZ MRI can improve the accuracy and reproducibility in CBF maps by reducing the artifacts due to $B_0$-inhomogeneity, and therefore avoid potential misdiagnosis associated with conventional ASL MRI. In addition, the improved reproducibility can greatly benefit longitudinal and inter-subject pre-clinical and clinical studies. In one particular example of a clinical application. TADDZ MRI can differentiate the subtle CBF difference in Alzheimer's disease (AD) brains due to ApoE-4 genotype with statistical significance. Other advantages and implementations are enabled as well.

The methodology of TADDZ includes acquiring a set of ASL MRI target data of a target region, acquiring a set of ASL MRI control data of the target region, generating a Z-spectrum for each voxel in the imaging plane based on the target and control data, determining an estimated inhomogeneity of the $B_0$ magnetic field a the particular voxel, correcting the Z-spectrum based on the $B_0$ magnetic field inhomogeneity, and generating a corrected image of the target region of biologic material based on the corrected Z-spectrum for each voxel.

Figures 2A, 2B:
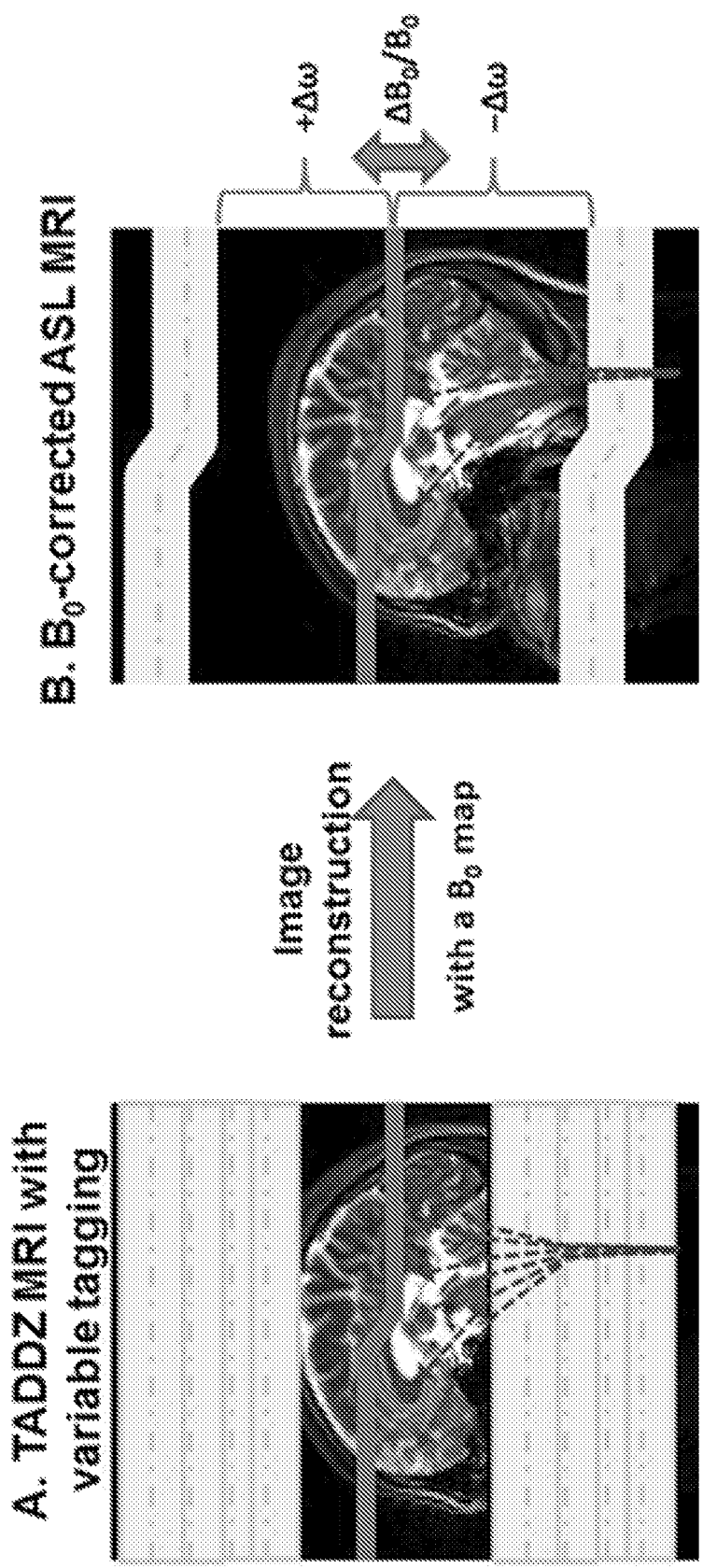
FIGS. 2A-B depict the use of tagging distance dependent Z-spectral (TADDZ) MRI to correct $B_0$ inhomogeneity-induced artifacts. In TADDZ MRI, the tagging distance from the imaging slice or the tagging frequency offset is varied, producing tagging-distance or frequency dependent Z-spectral image dataset (FIG. 2A). Along with a $B_0$ map, which in some embodiments is produced by the TADDZ MRI itself (similarly to water saturation shift referencing (WASSR) $B_0$ mapping) or, in some embodiments, by other conventional $B_0$-mapping methods, TADDZ MRI is able to eliminate $B_0$-inhomogeneity induced artifacts in the resulting CBF maps (FIG. 2B).

As illustrated in FIG. 2A, a plurality of ASL MRI data sets (i.e., data acquired through imaging) are acquired with tagging planes both upstream and downstream of the biological material (e.g., a human brain) in the imaging plane. One set of ASL MRI target data is acquired with tagging distances positioned upstream of the imaging plane, and an additional set of control data is acquired with tagging distances positioned downstream of the imaging plane. In this context, "upstream" and "downstream" indicate the position of the tagging plane relative to the target region of the biologic material in the imaging plane and according to the direction of fluid flow through the imaging plane. "Upstream" refers to the direction from which fluid is flowing (e.g., blood that has not yet entered the imaging plane), while "downstream" refers to the direction toward which fluid is flowing (e.g., blood that has passed through the imaging plane).

In some embodiments, acquiring the set of ASL MRI target data and control data entails imaging the biological material using an MRI system. Each of the target and control data can be acquired by an MRI system by applying an RF pulse to magnetically tag fluid at a predetermined tagging distance. The RF pulse can have a frequency offset with respect to a resonant frequency, which is indicative of the desired tagging distance of the tagged blood water from the imaging plane. A magnetic field gradient (e.g., an ASL gradient) is further applied by the MRI system in order to selectively apply the RF pulse in the tagging plane. To acquire the MRI data, RF signals are further received from the target region of biologic material. The data can be represented in spatial terms according to discrete voxels. The intensity of the received RF signals corresponding to each voxel of the imaging plane can yield information that can be used to construct target and control images of the target region of biologic material. As used herein, the term "voxel" defines data representing a discrete 3-dimensional volume element of the biologic material within the imaging plane. While the current method describes acquiring, storing, and processing data in terms of voxels, it is understood that the data could alternatively be represented in terms of pixels, with each pixel representing a discrete 2-dimensional space of the biologic material in the imaging plane. Accordingly, the terms voxel and pixel can be used interchangeably in this context.

After acquiring the sets of target and control data, the data can be plotted and analyzed to determine the estimated inhomogeneity of the $B_0$ magnetic field along the axial direction of the MRI system. Data analysis can include plotting the received RF signals at each voxel in order to determine how the position of the tagging plane (i.e., the tagging distance) effects the appearance of MS and DT artifacts in the imaging plane. To visualize these distance-dependent effects, a tagging distance dependent Z-spectrum (TADDZ) is generated for each voxel of the imaging plane based on the acquired ASL MRI target and control data. The Z-spectrum of each voxel represents the relationship between the RF signal measured at each voxel by the MRI system (y-axis) and the tagging distance or saturation frequency offset (x-axis) corresponding to each data point.

Using data from the tagging distance dependent Z-spectra for each voxel, TADDZ MRI is able to measure and eliminate $B_0$-inhomogeneity induced artifacts in the resulting CBF maps of the imaging plane, as shown in FIG. 2B. In particular, Z-spectrum analysis can allow for visualization and correction of tagging distance dependent artifacts likely introduced by the DS and MT effects of the tagging RF pulse. For instance, lateral shifts in the Z-spectrum and noise between data points can be caused by inhomogeneities in the $B_0$ magnetic field and the artifacts in the imaging plane that result from the tagging RF pulse under such inhomogeneities. By measuring deviations from the expected Z-spectrum, TADDZ can permit $B_0$ magnetic field mapping of the imaging plane and the estimation of the $B_0$ magnetic field inhomogeneities across the imaging plane.

In addition to enabling production of a $B_0$ map, TADDZ MRI is also capable of removing imaging artifacts through voxelwise (i.e., voxel by voxel) processing and correction of Z-spectrum data. For instance, detected magnetic field deviations at each voxel can be corrected by shifting the Z-spectrum of the voxel by the detected magnetic field variation. Likewise, fitting the Z-spectrum data with a curve can remove noise between data points and interpolate data according to a regression algorithm, e.g., a linear regression algorithm, a Lorentzian or super-Lorentzian algorithm, or any other curve fitting technique appreciated by one of skill in the art. Corrected and interpolated Z-spectrum data for each voxel can then be used to generate corrected ASL MRI target and control data sets, and a corrected image (i.e. a CBF map) can generated from this new data. TADDZ MRI methods thus provide a quantitative and consistent way of removing artifacts introduced by RF tagging of blood water in ASL MRI imaging. As a result, TADDZ may be capable of outperforming conventional ASL MRI in differentiating subtle CBF differences between disease states, subjects, and time points, therefore increasing clinical reliability of ASL MRI images.

As used herein, the singular forms "a", "an", and "the" include plural referents unless the context clearly dictates otherwise. For example, reference to a "nucleic acid" means one or more nucleic acids.

It is noted that terms like "preferably," "commonly," "conventionally", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of this invention.

For the purposes of describing and defining this invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

2. Example Methods

Embodiments disclosed herein by way of example provide example TADDZ MRI techniques applicable in an MRI system that includes capabilities for applying arterial spin labeling (ASL) gradients and further includes a mechanism for adjusting the tagging distance of the acquired ASL MRI images. As described above, an MRI system conventionally comprises hardware components including one or more gradient coils positioned about a bore of a magnet, an RF transceiver system, and an RF switch controlled by a pulse module to transmit RF pulses to and receive RF signals from an RF coil assembly. The received RF signals are also known as magnetic resonance (MR) signal data. An MRI system also conventionally includes one or more processors programmed to cause the system to apply to an object in the system various RF signals, magnetic fields, and field gradients for inducing spin excitations and spatial encoding in an object, to acquire MR signal data from the object, to process the MR signal data, and to construct an MR image (e.g., an image of the object generated based on the processed MR signal data). The one or more processors can include one or more general or special purpose processors, one or more forms of computer- or machine-readable memory, and one or more hardware and/or software interfaces for interacting with and/or controlling other hardware components of the MRI system.

Figure 3:
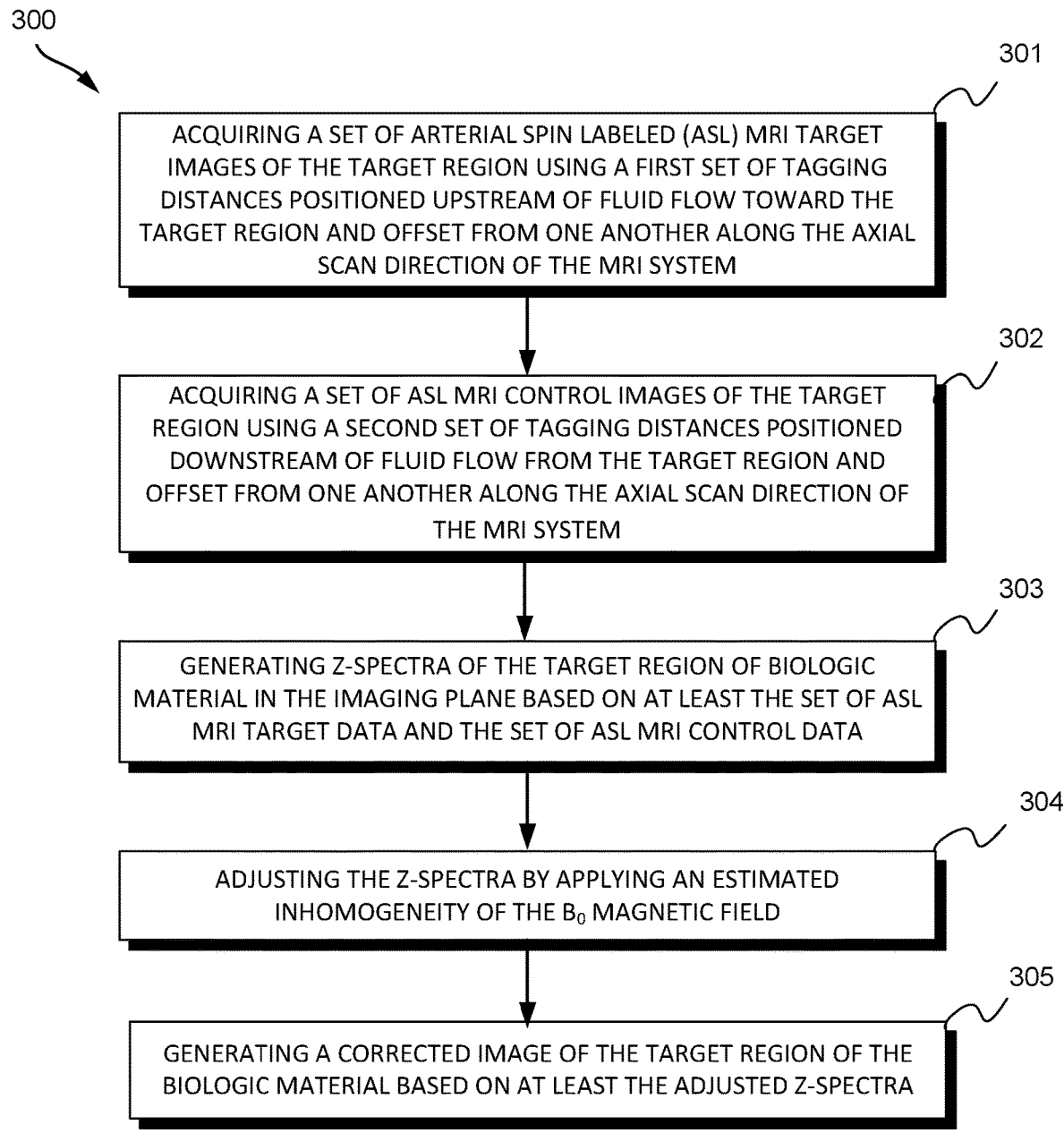
FIG. 3 shows a TADDZ method according to one example embodiment.

In an example embodiment, acquisition of tagging distance dependent Z-spectrum data in accordance with ASL MRI can be accomplished by way of a computer- or machine-implemented method configured for execution by the MRI processor. The steps of the method can augment and/or enhance convential ASL MRI operation in order to achieve the advantages of TADDZ. The steps can be implemented on a conventional MRI system having a $B_0$ magnetic field defining an axial scan direction. More particularly, an example method can be implemented as machine language (e.g., programmed) instructions that, when executed by the one or more processors of an MRI system, cause the MRI system to carry out the various operations and functions described herein. Further, the machine language instructions can be stored on a non-transitory computer-readable medium, such that the instructions can be accessed and executed by an MRI system, as described. FIG. 3 is a flowchart illustrating such an example method 300 used for characterizing a target region of biologic material in an imaging plane of a magnetic resonance imaging system.

At step 301, a set of ASL MRI target data of the target region is acquired. The set of ASL MRI target data is acquired using a first set of tagging distances positioned upstream of fluid flow toward the target region offset from one another along the axial scan direction of the MRI system. At step 302, a set of ASL MRI control data of the target region is acquired. The set of ASL MRI control data is acquired using a second set of tagging distances positioned downstream of fluid flow from the target region, wherein the tagging distances are offset from one another along the axial scan direction of the MRI system In some embodiments, steps 301 and 302 of method 300 include imaging the target region of biologic material using an MRI system to acquire a set of ASL MRI images. Each of the sets of target data and control data can be acquired by imaging the target region of biologic material in the imaging plane using conventional ASL MRI methods. Acquiring the set of ASL MRI target data includes applying a respective target radiofrequency (RF) pulse to magnetically saturate the fluid at each respective tagging distance of the first set of tagging distances, and, for each respective applied target RF pulse, receiving an MRI target signal from the imaging plane. Acquiring the set of ASL MRI control data includes applying a respective control RF pulse to magnetically saturate the fluid at each respective tagging distance of the second set of tagging distance, and, for each respective applied control RF pulse, receiving an MRI control signal from the imaging plane.

In the set of target images, fluid (e.g., blood or, more specifically, blood water) is tagged in a tagging plane positioned upstream of fluid flow toward the target region of the biological material. The tagging distance or frequency offset is adjusted between successive images, such that the target RF pulse magnetically saturates the fluid at each of the first range of tagging distances. After magnetically saturating the fluid, an MRI target signal (e.g., an RF signal) is received from the biological material in the imaging plane. The set of ASL. MRI target data could therefore represent the relative RF signal intensity received from the biological material at each voxel in the imaging plane for target images acquired at each of the first set of tagging distances.

Similarly, the set of ASL MRI control images are acquired by tagging blood water in variable tagging planes positioned downstream of the imaging plane at equal and opposite tagging distances from the imaging plane as compared to the tagging distances of the tagging planes of the ASL MRI target images. The tagging distance or frequency offset is adjusted between successive images, such that the control RF pulse magnetically saturates the fluid at each of the second range of tagging distances. After magnetically saturating the fluid, an MRI control signal (e.g., an RF signal) is received from the biological material in the imaging plane. The set of ASL MRI control data could represent the relative RF signal intensity received from the biological material at each voxel in the imaging plane for control images acquired at each of the second set of tagging distance.

As described above, spatially selective RF pulses are applied by the MRI system in order to magnetically saturate (i.e., tag) the fluid before image acquisition. The target and control RF pulses are applied by the MRI system in tagging planes at varying distances relative to the imaging plane defined by the first and second sets of tagging distances. Such saturating RF pulses are configured to invert the magnetization of the blood water in the tagging plane relative to the surrounding biological material, i.e. in order to impart magnetic contrast in the blood. The RF pulses correspond to respective frequency offsets, which, in some embodiments, are indicative of the desired tagging distance (e.g., the first and second sets of tagging distances) from the imaging plane. A magnetic field gradient (e.g., an ASL gradient) can also be applied by the MRI system. The gradient and frequency offset can be varied in order to selectively apply the RF pulse at the desired tagging distance, with a desired tagging gap value (i.e., a distance between successive tagging planes) or with a desired tagging plane thickness.

Each respective target RF pulse corresponds to a respective target frequency offset with respect to a resonant frequency, while each respective control RF pulse corresponds to a respective control frequency offset with respect to the resonant frequency. In some example embodiments, the resonant frequency is the resonant frequency of hydrogen nuclei located at the imaging plane. The resonant ("Larmor") frequency can be determined based on the localized magnetic field strength in the MRI system. For hydrogen nuclei in a typical 1.5 Tesla $B_0$ magnetic field of an MRI system, the resonant frequency is approximately 64 MHz. The tagging distances of the respective target and control RF pulses can be varied by adjusting a frequency offset of the RF pulses with respect to the resonant frequency in order to match the resonant frequency at the desired tagging distance.

In accordance with example embodiments, each of the first and second sets of tagging distances includes tagging distances at a number of positions relative to the imaging plane. In one embodiment, the first set of tagging distances includes at least two tagging distances upstream of the imaging plane. Likewise, the second set of tagging distances includes at least two tagging distances downstream of the imaging plane. However, data could be acquired with any number of tagging distances in order to, e.g., increase resolution of the Z-spectrum and/or more precisely map magnetic field inhomogeneities in the imaging plane. Successive tagging distances in the first and second set of tagging distances can be offset by a predetermined distance (i.e., a tagging gap value), for instance, 0.5 mm, 1 mm, 2.5 mm, 5 mm, or some other distance. In some embodiments, successive tagging distances of the first and second set can be varied by an amount related to the thickness of the tagging plane (i.e., such that successive tagging planes overlap, such that a successive tagging planes are a predetermined distance apart, such that the tagging gaps result in a desired center slice off-resonance, or for some other reason).

In accordance with example embodiments, the first set of tagging distances and the second set of tagging distances is positioned at equal and opposite distances from the imaging plane. In other words, each tagging distance of the first set is at a respective offset upstream from the imaging plane, and is paired with a corresponding tagging distance of the second set at an equal respective offset downstream from the imaging plane. In some embodiments, the first set of tagging distances and the second set of tagging distances range from about 0.001 cm to about 100 cm from the imaging plane, corresponding to respective frequency offsets with respect to the resonant frequency. However, in other examples the first set of tagging distances and the second set of tagging distances range from about 0.01 cm to about 50 cm, from about 0.01 cm to about 20 cm, from about 0.01 cm to about 10 cm, from about 0.1 cm to about 10 cm, from about 1 cm to about 10 cm, or some other range. However, any desired tagging distances and/or frequency offsets can be implemented without departing from the scope of this disclosure. It would be well understood by one of ordinary skill in the art how to choose tagging distances and/or frequency offsets appropriate for a particular MRI experiment, and to adjust the frequency offsets of the first and second sets of tagging distances in order to magnetically tag fluid at the desired tagging distance.

Acquiring each set of ASL MRI target data and control data further includes receiving an RF signal from the target region of biologic material in the imaging plane. The received RF signal can be measured and/or stored as an array of signal intensities received from corresponding to voxels in the imaging plane. The intensity of the received RF signals at each voxel of the imaging plane can yield information that can be used to construct target and control images of the target region of biologic material. For instance, the RF signal can be analyzed to provide physiological information relating to the target region of the biologic material, an amount of fluid flow or perfusion in the biologic material, a degree of magnetic contrast, and other information.

Figure 4:
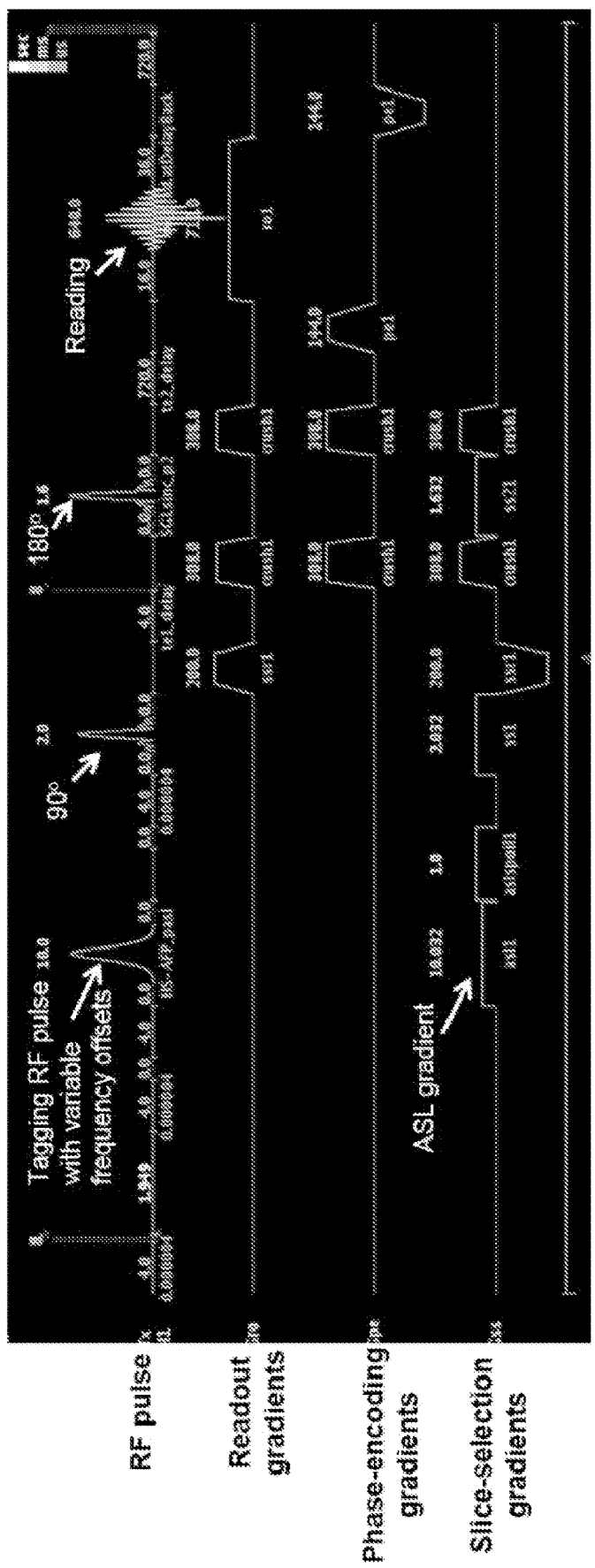
FIG. 4 is an exemplary TADDZ MRI pulse sequence diagram.

As illustrated in FIG. 4, the applied RF pulses can be encoded in a pulse sequence of the MRI system. Each RF pulse in the pulse sequence can have a frequency offset with respect to a resonant frequency. The tagging distance of the RF pulse can be specified by adjusting the frequency offset in order to match the Larmor frequency at the desired tagging distance. Gradients, such as ASL gradients (i.e., "slice-selection gradients"), can similarly be encoded in the pulse sequence of the MRI system. The gradients can be configured to apply an additional magnetic field in the MRI system that varies linearly over space. Such gradients can be applied concurrently with the target and control RF pulses in order to allow for additional spatial control of the tagging planes, in order to produce a tagging plane with the desired tagging distance, in order to produce a desired slice thickness, or some other characteristic. The positions of the first set of tagging distances and the second set of tagging distances relative to the imaging plane can be defined by the frequency offset of the associated RF pulse and any corresponding ASL gradient in the pulse sequence. Accordingly, an ASL gradient or frequency offset of the RF pulse can be varied in order to, e.g., produce tagging distance dependent Z-spectral data in each of the target and control data sets.

Returning to FIG. 3, the method 300 further includes jointly analyzing and correcting the set of ASL MRI target data and the set of ASL MRI control data. At step 303, a Z-spectrum is generated of the target region of biologic material in the imaging plane. Generation of the Z-spectrum is based on at least the set of ASL MRI target data and the set of ASL MRI control data. At step 304, the Z-spectra are adjusted by applying an estimated inhomogeneity of the $B_0$ magnetic field. Finally, at step 305 of the method, a corrected image of the target region is generated based on at least the adjusted Z-spectra. Data analysis according to steps 303-305 proceeds voxelwise. In other words, data from both the target and control data sets corresponding to a particular voxel is assembled to generate Z_spectra and the Z-spectra of each voxel is corrected individually. Later, corrected data from each voxel in the imaging plane can be assembled to produce a corrected image of the target region.

In accordance with example embodiments, generating the Z-spectrum in each respective voxel comprises determining, as a function of tagging distances of the first and second sets, a radiofrequency (RF) signal intensity received from the respective voxel. Determining the RF signal intensity received from the respective voxel can include identifying, from the set of ASL MRI target data and control data acquired at the first and second tagging distances, data acquired from a portion of the target region of biologic material corresponding to the voxel within in the imaging plane. Generating the Z_spectrum could include plotting the RF signal intensity received from the particular voxel with respect to the first set of tagging distances and the second set of tagging distances, so as to create a tagging distance-dependent visualization of the signal intensity. In other embodiments, the Z-spectrum can be plotted with respect to a frequency offset of the RF pulses used to produce the target and control data. An example Z-spectrum plot is illustrated in FIG. 5A, where the relative ASL signal intensity (%) is plotting against the saturation frequency offset (ppm) of the respective target and control RF pulses. The frequency offset of the saturating RF pulse is generally related to the tagging distance of the tagging plane, and, in the context of plotting the Z-spectrum and analyzing the TADDZ data, frequency offset and tagging distance can be used interchangeably.

An observed shift in the Z-spectrum indicates that the $B_0$ magnetic field at the particular voxel is shifted, with the shift in the Z-spectrum being proportional to the magnetic field inhomogeneity. (i.e., $\Delta B_0$). Accordingly, adjusting the Z-spectra by applying the estimated inhomogeneity of the $B_0$ magnetic field could include generating a Z-spectrum of the target region of biologic material in each respective voxel of the imaging plane (as described above), and determining an estimated inhomogeneity of the $B_0$ magnetic field in the imaging plane for each voxel in the imaging plane. Determining the estimated inhomogeneity of the $B_0$ magnetic field for each respective voxel entails determining a shift of the Z-spectrum of the voxel, wherein the shift is related to the $B_0$ magnetic field inhomogeneity at the particular voxel. This enables the tagging distance dependent Z-spectrum (TADDZ) data to map the $B_0$ magnetic field inhomogeneities at each voxel in the imaging plane. In such embodiments, method 300 could further include generating an image of the estimated inhomogeneity of the $B_0$ magnetic field in the imaging plane (i.e., a $\Delta B_0$ map). As described above, such an image is based on at least the determined shift in the Z-spectrum data at each voxel. Optionally, the image could then be displayed on an image display device (e.g., a remote computing device, a display associated with the MRI system, or some other image display device). In other embodiments the estimated inhomogeneity of the $B_0$ magnetic is determined by other $B_0$ mapping techniques, e.g., water saturation shift referencing (WASSR).

Adjusting the Z-spectra by applying the estimated inhomogeneity of the $B_0$ magnetic field also includes adjusting the Z-spectrum in each respective voxel according to the estimated inhomogeneity of the $B_0$ magnetic field in the respective voxel. As described previously, inhomogeneities in the magnetic field can manifest as lateral shifts in the Z-spectrum. Accordingly, adjusting the Z-spectrum in each respective voxel includes shifting the Z-spectrum in each respective voxel by an amount related to the estimated inhomogeneity in the $B_0$ magnetic field at the voxel (i.e., the amount determined by TADDZ or WASSR $\Delta B_0$ mapping).

In some embodiments, adjusting the Z-spectrum in each respective voxel in the imaging plane also includes fitting the respective Z-spectra to curve. Fitting the Z-spectrum data to a curve produces a trend line that allows for interpolation of the data between adjacent TADDZ data points. In other words, fitting the Z-spectrum to a curve generates new y-axis RF signal intensity values along the curve corresponding to each x-axis tagging distance value, thereby interpolating the TADDZ data. This effectively estimates the RF signal intensity at any number of tagging distances and/or frequency offsets between the measured data points, i.e., to simulate the acquisition of additional target and control data for a voxel. In some embodiments, the curve could be a linear trend line or a noise resilient linear regression algorithm, e.g., a Theil-Sen algorithm. However, other more complex fittings like Lorentzian, super-Lorentzian, or multi-component fittings can alternatively be used.

Once Z-spectra have been generated and adjusted based on the $\Delta B$ at each voxel, a corrected image of the target region of biologic material is generated based on at least the corrected Z-spectrum for each voxel. To generate the corrected image, a new set of corrected ASL MRI target data is generated for a desired tagging distance for each voxel in the imaging plane based on at least the adjusted Z-spectrum of the voxel. Additionally, a set of corrected ASL MRI control data is generated for a desired tagging for each voxel in the imaging plane based on at least the corrected Z-spectrum of the voxel. For each voxel, corrected data is generated by determining the estimated RF signal intensity at the desired tagging distance on the adjusted (i.e., shifted and/or interpolated) Z-spectrum of the voxel. The desired tagging distance could be any tagging distance selected by a user of the method for creation of the corrected image, for instance, any of the tagging distances of the first set or second set of tagging distances. Because the Z-spectra have likely been laterally shifted from their original (i.e., pre-correction) location, the RF signal intensity at the desired tagging distance may be in between data points. Thus, the corrected ASL MRI target and control data can be estimated by the RF signal intensity at the fitted curve. The same desired tagging distance should be used to generate both the corrected target and control data for the voxel, and for all other voxels in the imaging plane. In this context, the "same" desired tagging distance refers to a tagging distance that is a uniform distance away for the imaging plane, i.e., such that the corrected ASL MRI data points are all generated at the same desired tagging distance upstream of the imaging plane, while the corrected ASL MRI data points are all generated at the same desired tagging distance downstream of the imaging plane. For instance, if the desired tagging distance is 10 mm, corrected control data is generated for a tagging distance 10 mm upstream of the imaging plane for the target data and control data is generated for a tagging distance 10 mm downstream of the imaging plane based on the adjusted Z-spectra.

Generating a corrected image of the target region further includes, for each voxel in the imaging plane, determining a signal difference between the corrected target and corrected control data. Determining a signal difference entails subtracting the corrected ASL MRI control data from the corrected ASL MRI target data at the desired tagging distance for each voxel. As described previously, the set of ASL MRI target data is acquired by tagging blood water in tagging planes positioned upstream of the imaging plane, such that signal from the tagged blood is present in the acquired target data. Conversely, the set of ASL MRI control images is acquired after tagging blood water in tagging planes positioned downstream of the imaging plane, such that the tagged blood flows away from the imaging plane and the signal is not present in the control data. Accordingly, subtracting the control data from the target data for each voxel produces an RF signal difference that represents the presence or perfusion of blood through the voxel.

Generating a corrected image of the target region further includes generating a corrected image of the target region of biologic material in the imaging plane based on the signal difference at each voxel in the imaging plane. The image could include, for instance, a relative cerebral blood flow (rCBF) map of the target region. However, in other embodiments, a quantitative absolute CBF maps can be generated based on at least one of the target images, at least one of the control images, as well as other parameters, e.g., $T_1$ values of the blood and other tissues in the biologic material, and the tagging efficiency. Relative cerebral blood flow (rCBF) has a solution expressed analytically as:

$$rCBF = 100\% * \frac{(S_{ctr} - S_{tar})}{S_{ctr}}$$

$S_{ctr}$ is a parameter corresponding to the RF signal of the control image, while $S_{tar}$ is a parameter corresponding to the RF signal received in the target image with a tagging distance equal and opposite the imaging plane. According to some embodiments, generating the corrected image of the target region based on the signal difference at each voxel in the imaging plane includes inputting the corrected target and control data for each voxel into the above rCBF equation. The calculated rCBF at each voxel in the imaging plane can then be assembled into an image in order to visualize perfusion through the biological material in the imaging plane.

In some embodiments, analysis of the sets of target and control data according to steps 303-305 of the method 300 occurs on one or more processors of the system (e.g., a MRI system). In such examples, data correction can be accomplished by way of a customized imaging program on the system (e.g., a program stored in a memory of the system). The customized imaging program could be configured to jointly analyze the sets of ASL MRI target and control data and/or generate a corrected image of the target region in the imaging plane according to the TADDZ protocol described in method 300. Additionally or alternatively, the method 300 could include transmitting the target data and control data to a remote system (e.g., a remote computing device or a server) configured to jointly analyze the target and control data to generated corrected data sets. The remote system could then optionally transmit the corrected data to the MRI system, to a server, or to some other remote system.

Optionally, method 300 also includes displaying the corrected image of the target region on an image display device (e.g., a display of the MRI system, a display of a remote computing device, or a display of some other remote system). In some embodiments, the corrected image is also transmitted to a remote device (e.g., a remote computing device, a server, a device associated with hospital personnel or imaging technicians, etc.).

In accordance with example embodiments, the MRI system could include any suitable magnetic resonance imaging system configured to acquire ASL MRI images. In various embodiments, the method can be implemented on an MRI system based on Signal Targeting with Alternative Radio frequency (STAR) methodology, continuous arterial spin labeling (CASL), pseudo continuous ASL (PCASL), or some other arterial spin labeling technique.

Additionally, the biologic material could be neural tissue, such as a human brain. However, the biologic material of the method could be any range of human or non-human tissues, for instance, cardiac tissue, vasculature, bone tissue, spinal cord tissue, or some other tissue.

It will be appreciated that the example method steps 301-305 of the example embodiment of TADDZ can be embodied as executable instructions stored on a non-transitory computer- or machine-readable medium, such as magnetic disk, CD-ROM, or the like. The instructions, when executed by one or more processors of a system (e.g., a MRI system having a $B_0$ magnetic field defining an axial scan direction) can cause the MRI system to carry out the operations of the method 300. In such embodiments, acquiring the set of ASL MRI target images of the target region includes acquiring the set of ASL MRI target images from ASL MRI data previously measured and provided for storage by the MRI system (i.e., archived data saved in a memory of the system). Similarly, acquiring the set of ASL MRI control images of the target region can include acquiring the set of ASL MRI control images from the ASL MRI data previously measured and provided for storage by the MRI system.

It will also be appreciated that the method steps described above can be modified or rearranged, and that additional steps can be added, without changing the scope or spirit of example embodiments herein.

3. Example Analytical Description

Without being limited to any theory of the underlying basis for the invention one of ordinary skill will appreciate the following features of the TADDZ methods set forth herein.

As noted above, inhomogenous $B_0$ magnetic fields in an MRI system can result in nonuniform appearance of tagging artifacts in the ASL MRI target images and control images. TADDZ spectrum is affected by a several mechanisms, including direct saturation (caused by tagging RF pulses), semi-solid magnetization transfer, and blood flow effects. In some cases, Up-field Nuclear Overhauser Enhancement (NOE) and down-field CEST effects can also contribute artifacts to ASL MRI imaging. Analyzing the tagging distance dependent Z-spectrum (TADDZ) data of the acquired images can provide a quantitative and systematic approach for correcting these magnetic field variances in ASL-MRI images.

Figure 5:
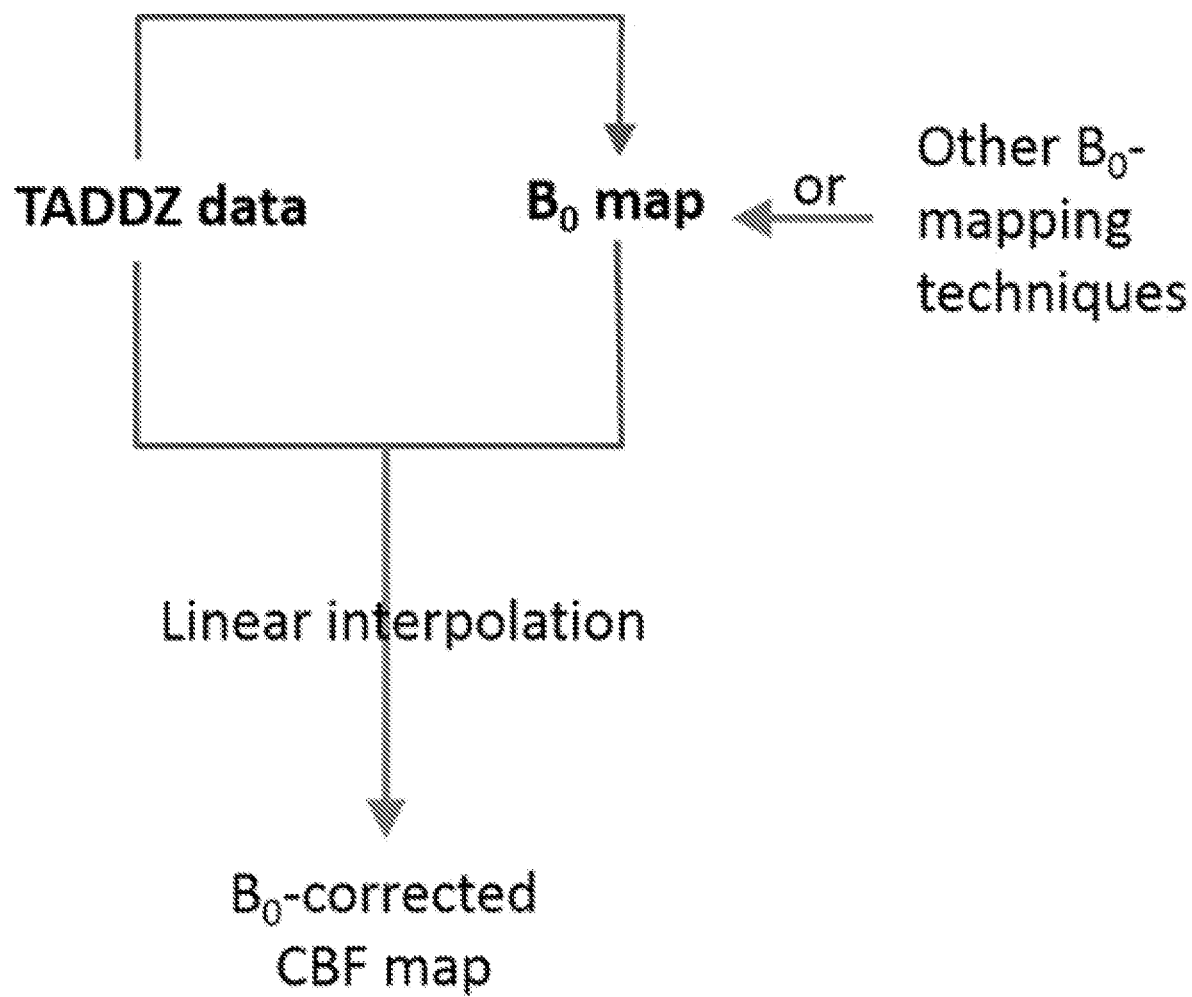
FIG. 5 depicts a flowchart of an exemplary TADDZ ASL MRI imaging processing algorithm according to one example embodiment.

As illustrated in FIG. 5, data and/or image analysis can include mapping of the $B_0$ magnetic field inhomogeneities of the imaging plane and/or linear interpolation of TADDZ data. In some embodiments, the $B_0$ map is produced by determining Z-spectrum shifts in the TADDZ data of the acquired target and control data as described previously. However, in other embodiments a $B_0$ map of the imaging plane can be generated by other B mapping techniques, e.g., water saturation shift referencing (WASSR).

In some cases, spectral data is collected, plotted, analyzed, and/or corrected individually for each voxel. This allows TADDZ to account for voxel-specific $B_0$ magnetic field variations across the imaging plane. Such inhomogeneities in the $B_0$ magnetic field may be visible as, for instance, deviations from an expected linear trend or lateral shifts in the Z-spectrum of a particular voxel of the imaging plane.

Figure 6:
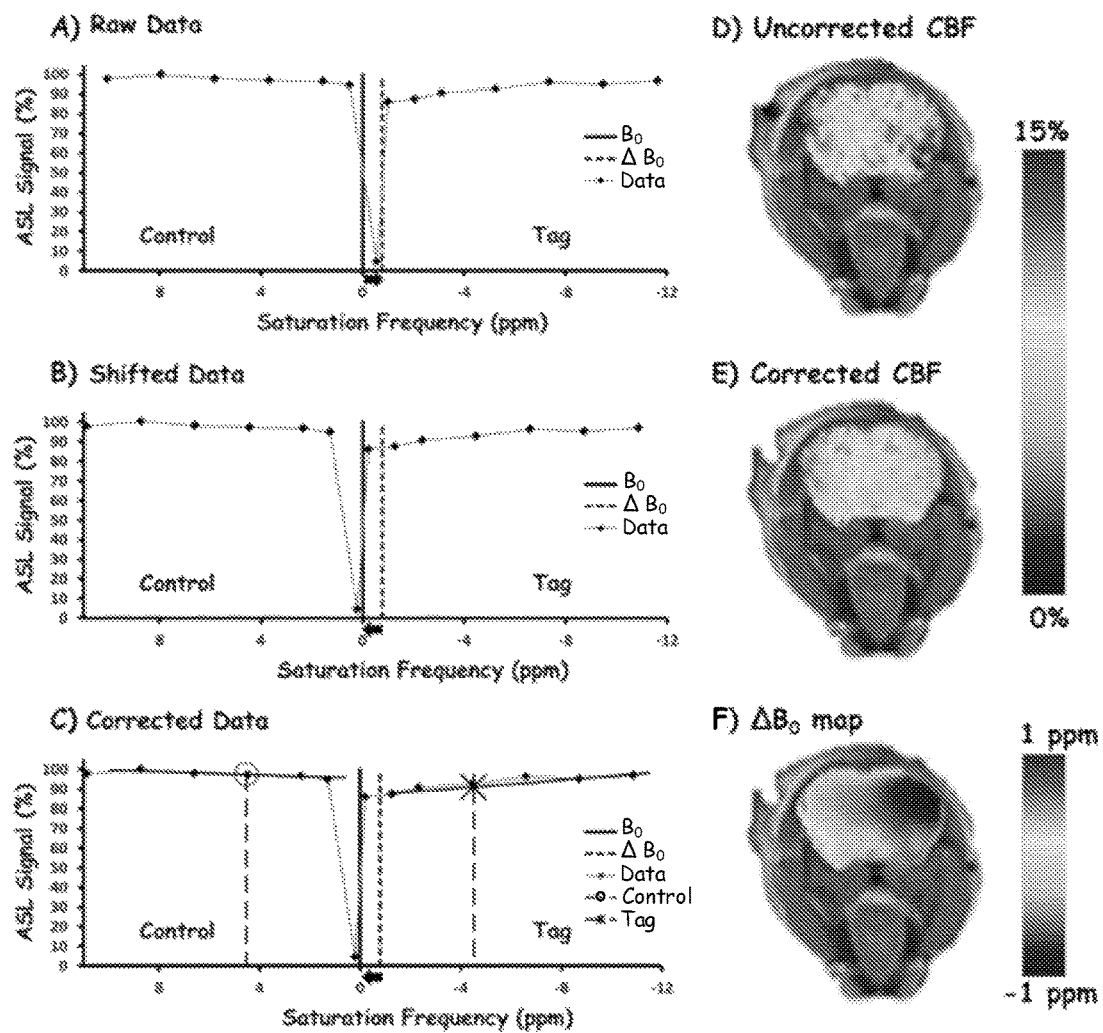
FIG. 6 shows representative tagging distance dependent Z-spectral (TADDZ) signals and relative cerebral blood flow (rCBF) maps. (A) shows a TADDZ from a pixel plotted against tagging distances (converted to ppm). A −0.8 ppm $B_0$ inhomogeneity is observed from this pixel. Image reconstruction to obtain B-corrected signals by unshifting according to the $B_0$ inhomogeneity (B) then interpolating signals at intended tagging distance (C). The O and X markers are the signal that was intended to be acquired. The corrected values are determined using linear regression (solid black lines) and interpolation. Sample rCBF maps before correction (D) after correction (E) and the corresponding $\Delta B_0$ map (F).

As shown in FIG. 6, (A-C), representative tagging distance dependent Z-spectral (TADDZ) signals from each voxel in the imaging plane can be plotted relative to the saturation frequency offset (ppm) of the tagging RF pulse used to acquire the image data. The saturation frequency offset is related to the tagging distance of each image, and can be converted back and forth from the tagging distance for data analysis. FIG. 6(A) illustrates an example Z-spectrum of a voxel, for example, a voxel corresponding to a particular location in the imaging plane and represented in the acquired sets of ASL MRI target and control data. Points plotted on the right ("tag") side of the x-axis represent data points for a particular voxel in the set of ASL MRI target data, i.e., data taken with tagging planes positioned upstream of fluid flow from the target region of the biologic material. These data points represent RF signals received from the biological material in the imaging plane, including added signal from tagged blood water in the imaging plane. Points on the left ("control") side represent data points corresponding to the same voxel in the set of ASL MRI control data, i.e., data taken with tagging planes positioned downstream of fluid flow from the target region of the biologic material, such that blood is not present in the control images. The relative difference in signal between the "tag" and "control" data points at equal and opposite frequency offsets, in theory, is indicative of the signal difference due to tagged blood perfusing through the target region at the particular voxel in the imaging plane.

As described previously, tagging RF pulses applied in the tagging plane can result in direct saturation and magnetization transfer effects in the imaging plane, among other signal effects and artifacts. As seen in FIG. 6, (A-C), these effects can result in dramatic and sudden dips in the signal intensity in the Z-spectrum as the saturation frequency approaches zero. Under a homogenous $B_0$ magnetic field, this dip would be expected to occur when the tagging plane is nearest to the imaging plane, i.e., when the tagging distance and/or saturation frequency offset is nearest zero. However, under an inhomogenous $B_0$ magnetic field, these effects may be more pronounced at some other tagging distance and/or saturation frequency. For instance, FIG. 6(A) shows a Z-spectrum shifted laterally to the right (indicated by the arrow). This shift in the Z-spectrum is indicative of the estimated inhomogeneity of the $B_0$ magnetic field at that voxel in the imaging plane.

In order to correct for the observed $B_0$ magnetic field inhomogeneity at the voxel, data analysis could include determining the shift in the Z-spectrum, and laterally shifting the Z-spectrum by the determined amount. For instance, FIG. 6(B) illustrates the Z-spectrum of panel (A) shifted such that the dip in the spectrum occurs where the tagging distance and/or saturation frequency offset is equal to zero, i.e., so as to correct the determined $B_0$ magnetic field inhomogeneity of the voxel. Shifts in the TADDZ spectrum for each voxel can then be used to determine the magnetic field shift (i.e., $\Delta B_0$) at each point in the imaging plane. Accordingly, an analysis of lateral shifts of the Z-spectrum of each voxel of the imaging plane allows for generation of a $\Delta B_0$ magnetic field map based on the acquired TADDZ data. An example of one such $\Delta B_0$ map is shown in FIG. 6(F).

Additional processing and analysis steps allow for further correction of TADDZ data inconsistencies. For instance, the Z-spectrum can also be fit to a curve in order to smooth out noise and interpolate the data points. As seen in FIG. 6(C), Z-spectrum data can be fit to a curve using a regression algorithm to produce a trend line between TADDZ data points. The regression algorithm could be a linear trend line or a noise resilient linear regression algorithm, e.g., a Theil-Sen algorithm. However, other more complex fittings like Lorentzian, super-Lorentzian, or multi-component fittings can alternatively be used. Furthermore, fitting the Z-spectrum to a curve allows for the interpolation of data and the estimation of signal amplitude at tagging distances and/or saturation frequencies between the measured data points, i.e., to simulate the acquisition of additional target and control data for a voxel. In other words, fitting the Z-spectrum to a curve generates new y-axis signal values along the curve that correspond to each x-axis tagging distance value, thereby interpolating the TADDZ data. This curve can then be used to estimate the corrected target and control data for the voxel at any desired tagging distance (or frequency offset).

A corrected image of the biologic material in the imaging plane can then be generated by calculating new target and control data based on the corrected Z-spectrum data for each voxel. For a desired tagging distance, a new target and control data point is determined by identifying the point on the corrected (i.e., shifted and interpolated) Z-spectrum corresponding to the desired tagging distance. For example, if a corrected image with a 10 mm tagging distance is desired, the interpolated and shifted Z-spectrum can be used to estimate the signal intensity at the 10 mm tagging distance of the control and target data sets (optionally converted to ppm). Corrected target and control values at the same tagging distance are then calculated for all remaining voxels in the imaging plane. The corrected Z-spectrum values for each voxel in the imaging plane are then input into a relative cerebral blood flow (rCBF) formula to develop a map of perfusion in the target region of the biologic material of interest. As discussed previously, the relative cerebral blood flow (rCBF) of a voxel has a solution expressed analytically as:

$$rCBF = 100\% * \frac{(S_{ctr} - S_{tar})}{S_{ctr}}$$

FIG. 6(D) illustrates an uncorrected relative cerebral blood flow (rCBF) image generated based on the raw target and control data. Corrected Z-spectrum data is then input into the same equation to construct a new image of the biological material in the imaging plane corrected for the estimated inhomogeneity of the B magnetic field. FIG. 6(E) illustrates an example rCBF image generated using the corrected (i.e., shifted and interpolated) data from FIG. 6(C).

In some embodiments, a customized image processing program can be used to reconstruct the rCBF image based on the TADDZ data. The customized image processing program could be included in instructions stores on the computer- or machine-readable memory (e.g., a memory of one or more processors of a MRI system, or some other system). The customized image processing program could be configured to determine the Z-spectrum of individual voxels in the imaging plane, shift the Z-spectrum of each individual voxel, interpolate the data, and calculate a corrected image of the target region in the imaging plane, and/or execute other functions.

4. Example Operation and Results

The Examples that follow are illustrative of specific embodiments disclosed herein and various uses thereof. They are set forth for explanatory purposes only and are not to be taken as limiting.

Example 1: $B_0$-Corrected ASL for Detection of Cerebral Blood Flow EFAD Mice

TADDZ spectra were used for $B_0$ correction in arterial spin labeling (ASL) to measure cerebral blood flow (CBF) in Alzheimer's disease (AD) mice that express either the apolipoprotein E 3 (ApoE3) or apolipoprotein E 4 (ApoE4) gene (EFAD mice). ApoE4 is the greatest genetic risk factor for sporadic AD, increasing risk up to 12-fold compared to ApoE3. Although the role of ApoE in AD is complex, data support that ApoE4 induces cerebrovascular dysfunction in AD patients, including reduced cerebral blood flow. This Example describes experiments investigating the use of TADDZ-$B_0$-corrected ASL to improve detection of CBF reduction due to ApoE4 in AD.

Materials and Methods

MRI acquisition. MRI was performed by acquiring a series of spin echo-based Signal Targeting with Alternating Radio frequency (STAR) datasets from a central slice of mouse brain on a 9.41 small-animal scanner with tagging gap values of 0, 2.5, 5, 10, 15, 20, and 25 mm. Given a slice thickness ($S_{thk}$) of 1 mm and an ASL tagging gradient ($G_{asl}$) of 0.4 gauss/cm these tagging gaps were converted into off resonances ($\Delta\omega$) in parts per million (ppm) as follows:

$$\Delta\omega = 1{,}000{,}000 \times (S_{thk}/2 + gap)G_{asl}/B_0, \quad (1)$$

resulting in center slice off-resonances of $\pm 0.2$, $\pm 1.3$, $\pm 2.3$, $\pm 4.5$, $\pm 6.6$, $\pm 8.7$, and $\pm 10.8$ ppm, where the sign reflects the up-field/down-field nature of the control and tag saturation, respectively. The signal at those different off resonances formed the TADDZ spectrum.

Other imaging parameters included (repetition time)/(echo time) (TR/TE)=2000/9.6 ms, post labeling delay=500 ms, field of view=25×25 mm², matrix size=64×64, and number of average=1. The acquisition time for a full TADDZ spectrum was about 4.2 min.

Field inhomogeneity, expressed in a $\Delta B_0$ map, was determined using water saturation shift referencing (WASSR) (see Kim et al., 2009, Magn. Reson. Med. 61(6):1441-50) images (from −1 ppm to +1 ppm with increment of 0.1 ppm) collected with a 100 ms saturation pulse of 0.47 µT using a single-shot Fast Low Angle Shot (FLASH) sequence (see Cai et al., 2012, Nature Medicine 18(2):302-6; Singh et al., 2012, Magn. Reson. Med. 68(2): 588-94; Cai et al., 2015, NMR Biomed. 28(1):1-8; Cai et al., 2014, Mol. Imaging Biol. 16(5):670-9). The acquisition time for WASSR was about 2 min.

Image processing. Relative CBF (rCBF) were computed before and after $B_0$ correction according to the following equation, $$rCBF = 100\% * \frac{(S_{ctr} - S_{tag})}{S_{ctr}}, \quad (1)$$

where $S_{ctr}$ and $S_{tag}$ are the signals with the intended tagging distance of 10 mm distal and proximal to the imaging slice, respectively.

$B_0$ correction was performed pixel-wise by shifting the acquired TADDZ spectrum data according to $\Delta B_0$ (FIG. 6, A-B) using interpolation based on a Thiel-Sen linear regression (see Sen, 1968, Journal of the American Statistical Association 63(324):1379-89) in the range ±2 to ±11 ppm to produce signals at the intended tagging distances of 10 mm (4.46 ppm), for control and tag respectively (FIG. 6, C).

In a systematically designed experiment, the $B_0$ map was intentionally shifted by 025, 0.5, and 1 ppm and compared rCBF maps before and after $B_0$ correction. (FIG. 6) (00891 Animal studies. To assess the CBF differences between the two phenotypically different groups of mice, conventional ASL and TADDZ MRI data were collected from male ApoE3 (n=5, 8 m) and ApoE4 (n=7, 8 m) AD mice. Uncorrected and corrected rCBF values were compared to reveal ApoE phenotype-induced CBF changes in the brain. Breeding and colony maintenance was conducted as described in Youmans et al., 2012, J Biol Chem. 287(50): 41774-86 and Thomas et al., 2016, Acta Neuropathol Commun. 4(1):11. EFAD mice were produced by crossing mice that express 5 Familial Alzheimer's disease (FAD) mutations (APP K670N/M671L+1716V+V7171 and PSI M146L+L286V) with ApoE-targeted replacement mice (Youmans et al., 2012, J Biol Chem. 287(50):41774-86). Therefore, EFAD+ mice are ApoE$^{+/+}$/5xFAD$^{+/-}$. Eight-month-old E3FAD+ and E4FAD+ mice were used. In this study only male EFAD mice were utilized for the purpose of consistency, as ApoE isoform-specific interaction with Aβ are known to be influenced by gender. Regions of interest (ROIs) in hippocampus and whole brain were manually drawn with reference to anatomic images.

Statistical analysis. In the MRI study of AD mice, unpaired two-tailed Student's t-test was used to compare the rCBF values from ApoE3 and ApoE4 mice. The difference was considered to be significant if p<0.05. Values were reported as Mean±Standard Deviation (std).

Results

Each TADDZ spectrum reflects the water signal for a single voxel within the imaging plane imaged using different tagging distances (or frequency offsets) as demonstrated in FIG. 6(A). The TADDZ signal can be affected by a few mechanisms, including direct saturation (or tagging), semi-solid magnetization transfer, and blood flow effects. Under homogeneous $B_0$ conditions, when the tagging gap is less than one mm, the tagging region overlaps with the imaging plane and the ASL tagging pulse directly interacts with the protons of the imaging slice, resulting in a minimal signal, i.e., a sharp dip in the TADDZ spectrum mainly due to the direct saturation effect.

Away from the dip in the TADDZ spectrum, the ASL tagging region moves away from the imaging slice. Accordingly, the signal increases due to reduced direct saturation and magnetization transfer effects. However, besides the influence from direct saturation and magnetization transfer effects, ASL contrast from blood flow also contributes to the signal attenuation in the proximal or down-field TADDZ spectrum. It is the difference between the up-field and down-field TADDZ spectral signals that provides the ASL contrast that reflects brain CBF assuming a homogenous imaging plane $B_0$ field, or $\Delta B_0$=0.

Under a homogenous B field, the nadir of a TADDZ spectrum points to the experimental frequency offset at 0 ppm (tagging distance of <0 mm). However, when $\Delta B_0$ is not 0 ppm, the entire TADDZ spectrum shifts proportionally to $\Delta B_0$ as demonstrated in FIG. 6(A). Without $B_0$ correction, a conventional ASL contrast computation is contaminated by asymmetric DS and MT effects. For each voxel, by shifting back the entire TADDZ spectrum with respect to $\Delta B_0$ (FIG. 6, B) and using linear interpolation of regional data (FIG. 6, C), the $B_0$-corrected ASL contrast was rendered at the intended tagging distance (or frequency offset). As demonstrated in FIG. 6(D-F), the conventional rCBF map (FIG. 6, D) was highly affected by $\Delta B_0$ map heterogeneities (FIG. 6, F), while such influence was minimized in the $B_0$-corrected rCBF map (FIG. 6, E).

Figure 7:
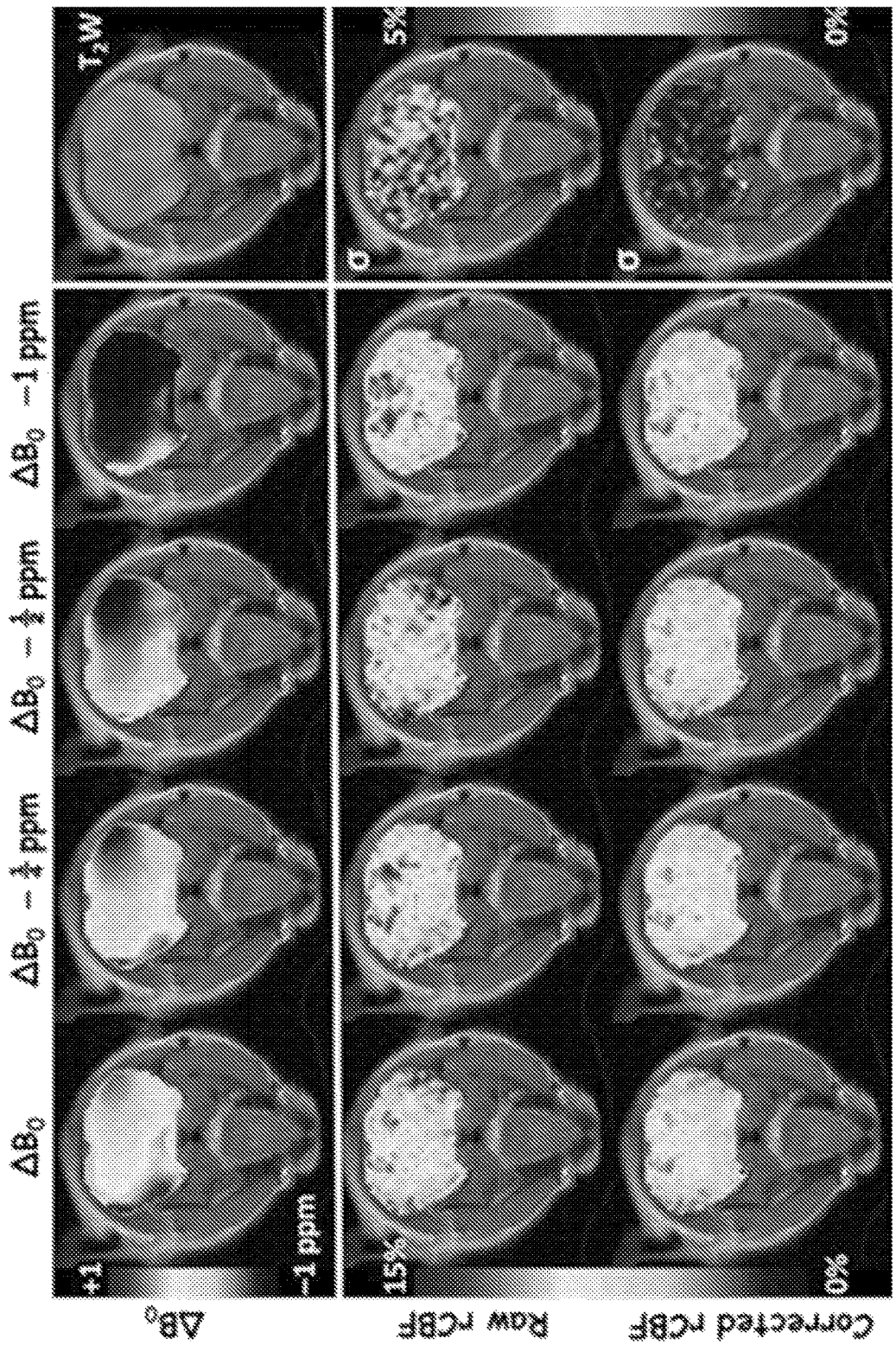
FIG. 7 shows correction of $B_0$ inhomogeneity induced artifacts using TADDZ MRI. The top row shows the $\Delta B_0$ maps. The middle row shows the uncorrected CBF maps produced from conventional ASL MRI, whereas the bottom row shows the $B_0$-corrected CBF maps from TADDZ MRI. The columns, from left, depict experiments in which $\Delta B_0$ is manually shifted by 0, 0.25, 0.5, and 1 ppm, respectively. The last column depicts the pixel-wise standard deviation (a)

A test-retest study was performed in which the original $\Delta B_0$ field was intentionally and systematically altered by adding progressively increased offsets (FIG. 7, top row). TADDZ datasets were collected, and both uncorrected rCBF maps (FIG. 7, middle row) and $\Delta B_0$ corrected rCBF maps (FIG. 7, bottom row) were produced. The top row shows the ΔB maps. The middle row of shows the uncorrected CBF maps produced from conventional ASL MRI, whereas the bottom row shows the $B_0$-corrected CBF maps from TADDZ MRI. The columns, from left, depict the experiments by manually shifting $\Delta B_0$ by 0, 0.25, 0.5, and 1 ppm, respectively. The right-most column of FIG. 7 shows voxel-wise standard deviation (σ) maps of the uncorrected and corrected rCBF maps. The upper right image is a T2-weighed image showing the brain anatomy. The α maps demonstrate that, whereas the uncorrected rCBF maps exhibit noticeable variations due to systematic variation of $\Delta B_0$, the AB correction greatly reduced such variation by a factor of 3.

Whereas the conventional CBF maps exhibited noticeable variations (σ) due to changes in $\Delta B_0$, TADDZ MRI produced $B_0$-corrected CBF maps that have negligible variations under different $\Delta B_0$ fields.

In a pre-clinical translational study, ApoE dependent AD mice (5xFAD with ApoE3 or ApoE4 genotype) were MRI scanned. Representative rCBF maps before and after $B_0$-correction are shown in FIG. 8(A). FIG. 8 illustrates representative brain images from a ApoE3 (top row) and ApoE4, (bottom row) mice. Columns from left to right are T2 weighted image, $\Delta B_0$, uncorrected (from conventional ASL MRI), and corrected rCBF maps (from TADDZ MRI), respectively. FIG. 8(B) illustrates a bar chart depiction of the rCBF differences between ApoE3 and ApoE4 mice, uncorrected (conventional ASL MRI, left) and corrected (TADDZ MRI, right) within the hippocampus (left chart) and whole brain (right chart). * p<0.05). The difference between the uncorrected rCBF was not significantly different between the ApoE3 vs ApoE4 within the hippocampus (8.0±0.9% vs 7.5±1.6%, p=0.31) and whole brain (6.0±1.0% vs 6.3±1.3%, p=0.35). However, the TADDZ-based correction improved the differentiation power by showing significantly higher rCBF in the ApoE3 versus ApoE4 within both the hippocampus (8.2±0.4% vs 7.20±0.8%, p<0.05) and the whole brain (6.7±0.4% vs 5.8±0.9%, p<0.05) (FIG. 8, B). Such differentiation was not made by conventional ASL MRI. In other words, TADDZ MRI has greatly improved the detection sensitivity and therefore significantly reduces sample size and cost required for preclinical and clinical applications.

DISCUSSION

Susceptibility variations between the head, neck, and body makes obtaining a homogeneous $B_0$ field in both the imaging and tagging regions during ASL MRI challenging, especially at ultra-high magnetic fields. In this Example, imaging plane $B_0$-inhomogeneity induced artifacts in ASL MRI were investigated, and a $B_0$-corrected ASL technique was developed using TADDZ spectra. The results indicate that image-plane $B_0$-inhomogeneity can lead to large variations in CBF maps. Along with enabling generation of a $B_0$ map, TADDZ MRI is able to eliminate $B_0$-inhomogeneity induced artifacts in the resulting CBF maps, demonstrating that TADDZ correction is effective in reducing test-retest variations. The applicability of TADDZ MRI to ASL correction was also demonstrated using AD mouse models. In these experiments, TADDZ MRI was able to differentiate the subtle CBF difference in Alzheimer's disease (AD) mice brains at 9.4 T with different ApoE genotypes. Such differentiation was not made using conventional ASL, MRI.

More specifically, the TADDZ MRI technique was applied to study CBF differences in mice with AD that express ApoE3 or ApoE4 genotype. Sporadic AD accounts for more than 95% of all cases and ApoE4 is the greatest genetic risk factor, increasing risk up to 15-fold compared to ApoE3 and affecting the age of AD onset. CBF changes serve as an imaging biomarker for metabolic changes due to ApoE4. As discussed above, TADDZ MRI with imaging plane $B_0$-corrected rCBF improved the consistency, enhancing the statistical power to differentiate ApoE phenotype dependent brain perfusion. ApoE4 mice were found to have reduced CBF compared to ApoE3 mice, consistent with the literature. Compared to ApoE3 mice, in male ApoE4 mice there is evidence of higher cerebrovascular leakiness which indicates capillary breakdown, and the deposition of amyloid beta (Aβ) in larger vessels (likely arterioles) as cerebral amyloid angiopathy (CAA). Thus, both capillary and arteriole dysfunction underlie the observed reduced CBF in male E4FAD mice.

These studies demonstrate, for the first time, the correction of asymmetric MT effects due to imaging-plane $B_0$ magnetic field inhomogeneity. By enabling removal of artifacts arising from static $B_0$ field inhomogeneity, TADDZ-based correction of B) enhances the robustness of CBF quantification, improves statistical power, and reduces clinical misdiagnosis.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. In a magnetic resonance imaging (MRI) system having a $B_0$ magnetic field defining an axial scan direction, a method for imaging a target region of biologic material in an imaging plane, the method comprising:
    acquiring a set of arterial spin labeled (ASL) MRI target data of the target region using a first set of tagging distances positioned upstream of fluid flow toward the target region and offset from one another along the axial scan direction of the MRI system;
    acquiring a set of ASL MRI control data of the target region using a second set of tagging distances positioned downstream of fluid flow from the target region and offset from one another along the axial scan direction of the MRI system;
    generating Z-spectra of the target region of biologic material in the imaging plane based on at least the set of ASL MRI target data and the set of ASL MRI control data;
    adjusting the Z-spectra by applying an estimated inhomogeneity of the $B_0$ magnetic field; and
    generating a corrected image of the target region of the biologic material based on at least the adjusted Z-spectra.

2. The method of claim 1, wherein acquiring the set of ASL MRI target data comprises:
    applying a respective target radiofrequency (RF) pulse to magnetically saturate the fluid at each respective tagging distance of the first set of tagging distances; and
    for each respective applied target RF pulse, receiving an MRI target signal from the imaging plane;
    and wherein acquiring the set of ASL MRI control data comprises:
    applying a respective control RF pulse to magnetically saturate the fluid at each respective tagging distance of the second set of tagging distances; and
    for each respective applied control RF pulse, receiving an MRI control signal from the imaging plane.

3. The method of claim 2, wherein each respective target RF pulse corresponds to a respective target frequency offset with respect to a resonant frequency,
    and wherein each respective control RF pulse corresponds to a respective control frequency offset with respect to the resonant frequency.

4. The method of claim 3, wherein the first set of tagging distances and the second set of tagging distances range from 1 cm to 10 cm.

5. The method of claim 1, wherein each tagging distance of the first set is at a respective offset upstream from the imaging plane, and is paired with a corresponding tagging distance of the second set at an equal respective offset downstream from the imaging plane.

6. The method of claim 1, wherein adjusting the Z-spectra by applying the estimated inhomogeneity of the $B_0$ magnetic field comprises:
    generating a Z-spectrum of the target region of biologic material in each respective voxel of the imaging plane;
    determining the estimated inhomogeneity of the $B_0$ magnetic field for each respective voxel of the image plane; and adjusting the Z-spectrum in each respective voxel according to the estimated inhomogeneity of the $B_0$ magnetic field in the respective voxel.

7. The method of claim 6, wherein generating the Z-spectrum in each respective voxel comprises determining, as a function of tagging distances of the first and second sets, a radiofrequency (RF) signal intensity received from the respective voxel.

8. The method of claim 6, wherein determining the estimated inhomogeneity of the $B_0$ magnetic field for each respective voxel of the image plane comprises determining a shift of the Z-spectrum, wherein the shift is related to a $B_0$ magnetic field inhomogeneity at the voxel.

9. The method of claim 8, further comprising:
generating an image of the estimated inhomogeneity of the $B_0$ magnetic field in the imaging plane based on at least the determined shift in the Z-spectrum at each voxel; and
displaying the image on an image display device.

10. The method of claim 6, wherein adjusting the Z-spectrum in each respective voxel comprises:
shifting the Z-spectrum in each respective voxel by an amount related to the estimated inhomogeneity of the $B_0$ magnetic field at the voxel; and
fitting the Z-spectrum to a curve.

11. The method of claim 1, wherein generating a corrected image of the target region comprises:
for each voxel in the imaging plane:
generating a set of corrected ASL MRI target data for a desired tagging distance based on at least the adjusted Z-spectrum;
generating a set of corrected ASL MRI control data for the desired tagging distance based on at least the adjusted Z-spectrum; and
determining a signal difference by subtracting the corrected ASL MRI control data from the corrected ASL MRI target data at the desired tagging distance; and
generating a corrected image of the target region of biologic material in the imaging plane based on the signal difference at each voxel in the imaging plane.

12. The method of claim 1, further comprising displaying the corrected image of the target region on an image display device.

13. The method of claim 1, wherein the biologic material comprises a human brain, and wherein the fluid is blood.

14. A non-transitory computer-readable medium having instructions stored thereon that, when executed by one or more processors or a magnetic resonance imaging (MRI) system having a $B_0$ magnetic field defining an axial scan direction, cause the MRI system to carry out operations including:
acquiring a set of arterial spin labeled (ASL) MRI target data of a target region of biologic material in an imaging plane using a first set of tagging distances positioned upstream of fluid flow toward the target region and offset from one another along the axial scan direction of the MRI system;
acquiring a set of ASL MRI control data of the target region using a second set of tagging distances positioned downstream of fluid flow from the target region and offset from one another along the axial scan direction of the MRI system;
generating Z-spectra of the target region of biologic material in the imaging plane based on at least the set of ASL MRI target data and the set of ASL MRI control data;
adjusting the Z-spectra by applying an estimated inhomogeneity of the $B_0$ magnetic field; and
generating a corrected image of the target region of the biologic material based on at least the adjusted Z-spectra.

15. The non-transitory computer-readable medium of claim 14, wherein acquiring the set of ASL MRI target data of the target region comprises acquiring the set of ASL MRI target data from ASL MRI data previously measured by the MRI system and provided for storage on the memory,
and wherein acquiring the set of ASL MRI control data of the target region comprises acquiring the set of ASL MRI control data from the ASL MRI data previously measured by the MRI system and provided for storage on the memory.

16. The non-transitory computer-readable medium of claim 15, wherein adjusting the Z-spectra by applying the estimated inhomogeneity of the $B_0$ magnetic field comprises:
generating a Z-spectrum of the target region of biologic material in each respective voxel of the imaging plane;
determining the estimated inhomogeneity of the $B_0$ magnetic field for each respective voxel of the image plane; and
adjusting the Z-spectrum in each respective voxel according to the estimated inhomogeneity of the $B_0$ magnetic field the respective voxel.

17. The non-transitory computer-readable medium of claim 14, wherein the biologic material comprises a human brain, and wherein the fluid is blood.

18. A magnetic resonance imaging (MRI) system comprising:
a $B_0$ magnetic field defining an axial scan direction;
one or more processors;
memory; and
machine-readable instructions stored in the memory that, when executed by the one or more processors, cause the MRI system to carry out functions including:
acquiring a set of arterial spin labeled (ASL) MRI target data of the target region using a first set of tagging distances positioned upstream of fluid flow toward the target region and offset from one another along the axial scan direction of the MRI system;
acquiring a set of ASL MRI control data of the target region using a second set of tagging distances positioned downstream of fluid flow from the target region and offset from one another along the axial scan direction of the MRI system;
generating Z-spectra of the target region of biologic material in the imaging plane based on at least the set of ASL MRI target data and the set of ASL MRI control data;
adjusting the Z-spectra by applying an estimated inhomogeneity of the $B_0$ magnetic field; and
generating a corrected image of the target region of the biologic material based on at least the adjusted Z-spectra.

19. The system of claim 18, wherein acquiring the set of ASL MRI target data comprises:
applying a respective target radiofrequency (RF) pulse to magnetically saturate the fluid at each respective tagging distance of the first set of tagging distances; and
for each respective applied target RF pulse, receiving an MRI target signal from the imaging plane;
and wherein acquiring the set of ASL MRI control data comprises:

applying a respective control RF pulse to magnetically saturate the fluid at each respective tagging distance of the second set of tagging distances, and for each respective applied control RF pulse, receiving an MRI control signal from the imaging plane.

20. The system of claim 18, wherein the biologic material comprises a human brain, and wherein the fluid is blood.

\* \* \* \* \*